United States Patent [19]
Bölin et al.

[11] Patent Number: 6,025,164
[45] Date of Patent: Feb. 15, 2000

[54] BACTERIAL ANTIGENS AND VACCINE COMPOSITIONS

[75] Inventors: Ingrid Bölin, Göteborg; Ann-Mari Svennerholm, Västra Frölunda, both of Sweden

[73] Assignee: Astra Aktiebolag, Sodertalje, Sweden

[21] Appl. No.: 08/669,560

[22] PCT Filed: Jun. 3, 1996

[86] PCT No.: PCT/SE96/00727

§ 371 Date: Jul. 12, 1996

§ 102(e) Date: Jul. 12, 1996

[87] PCT Pub. No.: WO96/38475

PCT Pub. Date: Dec. 5, 1996

[30] Foreign Application Priority Data

Jun. 1, 1995 [SE] Sweden .................................. 9502007
Mar. 21, 1996 [SE] Sweden .................................. 9601085

[51] Int. Cl.[7] .......................... C12P 21/06; C12N 15/00; C12N 5/00; C07H 21/04

[52] U.S. Cl. ..................... 435/69.3; 435/320.1; 435/325; 514/44; 536/23.7

[58] Field of Search .................... 530/300, 350; 536/23.7; 435/69.3, 320.1, 325, 7.1; 424/184.1, 200.1; 514/44

[56] References Cited

U.S. PATENT DOCUMENTS 5,420,014  5/1995  Cripps et al. .
5,538,729  7/1996  Czinn et al. .
5,721,349  2/1998  Cover et al. .
5,780,601  7/1998  Green et al. .

OTHER PUBLICATIONS

Reeck et al (Cell vol. 50, p. 667), Aug. 28, 1987.
Bolin et al (J. of Clin. Microbiology vol. 33(2) pp. 381–384), Feb. 1995.
Evans, et al., J. Bacteriol. 175, 674–683 (1993).
Luke, et al., Microbiology 141, 597–604 (1995).
Burgess et al (J. of Cell Biology vol. 111 Nov. 1990 pp. 2129–2138).
Lazar et al (Molecular & Cellular Biology vol. 8 No. 3 Mar 1988 pp. 1247–1252).
Salgaller et al (Cancer Immunol. Immunother. vol. 39 pp. 105–116 1994).
Tuffano et al (Infection & Immunity vol. 62 No. 4 Apr. 1994 pp. 1392–1399).
Bassler et al (Innumitat and Infection vol. 20 No. 3 Jul. 1992, Abstract).

*Primary Examiner*—Anthony C. Caputa
*Assistant Examiner*—Mark Navarro
*Attorney, Agent, or Firm*—White & Case LLP

[57] ABSTRACT

The present invention relates to recombinant polypeptides which constitute *Helicobacter pylori* surface-exposed antigens with an approximate molecular weight of 29 kDa. The invention furthermore provides nucleic acid molecules coding for the said polypeptides, as well as vectors and host cells comprising such nucleic acid molecules. The said recombinant polypeptides are useful for the diagnosis of *H. pylori* infections and for the manufacture of vaccine compositions which will elicit a protective immune response against such infections, said vaccine compositions being suitable for both therapeutic and prophylactic use.

8 Claims, 2 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1670 base pairs
      (B) TYPE: nucleic acid
      (C) STRANDEDNESS: double
      (D) TOPOLOGY: linear    (ii) MOLECULE TYPE: cDNA    (ix) FEATURE:
      (A) NAME/KEY: CDS
      (B) LOCATION: 793..1575

(ix) FEATURE:
      (A) NAME/KEY: mat_peptide (B) LOCATION: 793..1572

(xi) SEQUENCE DESCRIPTION: SEQ ID NO:1:

```
GATCCTATCG CGCCAAAGGT GGTATTAGGA ATAAGAGCTT GATTATTAAT CTCCCTGGTA      60

AGTCCAAAAA GTATTAGAGA ATGCTTAGAG GCGGTTTTTC CAGCGATTCC TTATTGCGTG     120

GATTTGATTT TAGGGAATTA CATGCAAGTG AATGAAAAAA ACATTCAAGC GTTTGCCCCC     180

AAACAATAAG GTAAAAAATG CCACTCACTC ATTTGAATGA AGAAAATCAA CCTAAAATGG     240

TGGATATAGG GGATAAAGAA ACCACTGAAA GAATCGCTCT AGCAAGCGGT CGTATCAGCA     300

TGAATAAAGA GGCTTATGAC GCTATTATCA ATCATGGCGT CAAAAAGGGT CCGGTATTAC     360

AAACTGCTAT TATTGCTGGG ATTATGGGGG CTAAAAAGAC AAGCGAACTC ATTCCCATGT     420

GCCATCCAAT CATGCTCAAT GGGGTGGATA TTGATATTTT AGAAGAAAAA GAGACTTGTA     480

GTTTTAAACT CTATGCGAGA GTCAAAACTC AAGCTAAAAC GGGCGTAGAA ATGGAAGCGC     540

TAATGAGTGT GAGCGTAGGG CTTTTAACCA TTTATGACAT GGTGAAAGCC ATTGATAAGA     600

GCATGACAAT TAGCGGTGTG ATGCTGGAAT ATAAAAGTGG AGGCAAAAGT GGGGATTATA     660

ACGCTAAAAA ATAGAAAAAG ACTGATAATC TAAAGATATT AGGGTAAAAT AACATTTTGA     720

CAACAAAAGC GTGTTGGTTG CTTCGGATTT GTTGTTATAG AAGTCTAAAA TATTACAATC     780

AAGGATAGAA CG ATG AGA GCA AAT AAT CAT TTT AAA GAT TTT GCA TGG         828
              Met Arg Ala Asn Asn His Phe Lys Asp Phe Ala Trp
                1               5                  10

AAA AAA TGC CTT TTA GGC GCG AGC GTG GTG GCT TTA TTA GTG GGA TGC        876
Lys Lys Cys Leu Leu Gly Ala Ser Val Val Ala Leu Leu Val Gly Cys
             15                  20                  25

AGC CCG CAT ATT ATT GAA ACC AAT GAA GTC GCT TTG AAA TTG AAT TAC        924
Ser Pro His Ile Ile Glu Thr Asn Glu Val Ala Leu Lys Leu Asn Tyr
         30                  35                  40

CAT CCA GCT AGC GAG AAA GTT CAA GCG TTA GAT GAA AAG ATT TTG CTT        972
His Pro Ala Ser Glu Lys Val Gln Ala Leu Asp Glu Lys Ile Leu Leu
     45                  50                  55                  60

TTA AGG CCA GCT TTC CAA TAT AGC GAT AAT ATC GCT AAA GAG TAT GAA       1020
Leu Arg Pro Ala Phe Gln Tyr Ser Asp Asn Ile Ala Lys Glu Tyr Glu
                 65                  70                  75

AAC AAA TTC AAG AAT CAA ACC GCG CTC AAG GTT GAA CAG ATT TTG CAA       1068
Asn Lys Phe Lys Asn Gln Thr Ala Leu Lys Val Glu Gln Ile Leu Gln
             80                  85                  90

AAT CAA GGC TAT AAG GTT ATT AGC GTA GAT AGC AGC GAT AAA GAC GAT       1116
Asn Gln Gly Tyr Lys Val Ile Ser Val Asp Ser Ser Asp Lys Asp Asp
         95                  100                 105

TTT TCT TTT GCA CAA AAA AAA GAA GGG TAT TTG GCG GTT GCT ATG AAT       1164
Phe Ser Phe Ala Gln Lys Lys Glu Gly Tyr Leu Ala Val Ala Met Asn
    110                 115                 120

GGC GAA ATT GTT TTA CGC CCC GAT CCT AAA AGG ACC ATA CAG AAA AAA       1212
Gly Glu Ile Val Leu Arg Pro Asp Pro Lys Arg Thr Ile Gln Lys Lys
125                 130                 135                 140

TCA GAA CCC GGG TTA TTA TTC TCC ACC GGT TTG GAC AAA ATG GAA GGG       1260
Ser Glu Pro Gly Leu Leu Phe Ser Thr Gly Leu Asp Lys Met Glu Gly
                145                 150                 155

GTT TTA ATC CCG GCT GGG TTT ATT AAG GTT ACC ATA CTA GAG CCT ATG       1308
Val Leu Ile Pro Ala Gly Phe Ile Lys Val Thr Ile Leu Glu Pro Met
            160                 165                 170

AGT GGG GAA TCT TTG GAT TCT TTT ACG ATG GAT TTG AGC GAG TTG GAC       1356
Ser Gly Glu Ser Leu Asp Ser Phe Thr Met Asp Leu Ser Glu Leu Asp
        175                 180                 185

ATT CAA GAA AAA TTC TTA AAA ACC ACC CAT TCA AGC CAT AGC GGG GGG       1404
```

```
Ile Gln Glu Lys Phe Leu Lys Thr Thr His Ser Ser His Ser Gly Gly
            190                 195                 200

TTA GTT AGC ACT ATG GTT AAG GGA ACG GAT AAT TCT AAT GAC GCG ATC        1452
Leu Val Ser Thr Met Val Lys Gly Thr Asp Asn Ser Asn Asp Ala Ile
205                 210                 215                 220

AAG AGC GCT TTG AAT AAG ATT TTT GCA AAT ATC ATG CAA GAA ATA GAC        1500
Lys Ser Ala Leu Asn Lys Ile Phe Ala Asn Ile Met Gln Glu Ile Asp
                    225                 230                 235

AAA AAA CTC ACT CAA AAG AAT TTA GAA TCT TAT CAA AAA GAC GCC AAA        1548
Lys Lys Leu Thr Gln Lys Asn Leu Glu Ser Tyr Gln Lys Asp Ala Lys
            240                 245                 250

GAA TTA AAA GGC AAA AGA AAC CGA TAA AAACAAATAA CGCATAAGAA              1595
Glu Leu Lys Gly Lys Arg Asn Arg *
            255                 260

AAGAACGCTT GAATAAACTG CTTAAAAAGG GTTTTTTAGC GTTCTTTTTG AGCGTGTATT      1655

TAAGGGCTGA TGATC                                                       1670

(2) INFORMATION FOR SEQ ID NO:2:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Ala Asn Asn His Phe Lys Asp Phe Ala Trp Lys Lys Cys Leu
1               5                   10                  15

Leu Gly Ala Ser Val Val Ala Leu Leu Val Gly Cys Ser Pro His Ile
            20                  25                  30

Ile Glu Thr Asn Glu Val Ala Leu Lys Leu Asn Tyr His Pro Ala Ser
        35                  40                  45

Glu Lys Val Gln Ala Leu Asp Glu Lys Ile Leu Leu Arg Pro Ala
    50                  55                  60

Phe Gln Tyr Ser Asp Asn Ile Ala Lys Glu Tyr Glu Asn Lys Phe Lys
65                  70                  75                  80

Asn Gln Thr Ala Leu Lys Val Glu Gln Ile Leu Gln Asn Gln Gly Tyr
                85                  90                  95

Lys Val Ile Ser Val Asp Ser Ser Asp Lys Asp Phe Ser Phe Ala
            100                 105                 110

Gln Lys Lys Glu Gly Tyr Leu Ala Val Ala Met Asn Gly Glu Ile Val
        115                 120                 125

Leu Arg Pro Asp Pro Lys Arg Thr Ile Gln Lys Lys Ser Glu Pro Gly
    130                 135                 140

Leu Leu Phe Ser Thr Gly Leu Asp Lys Met Glu Gly Val Leu Ile Pro
145                 150                 155                 160

Ala Gly Phe Ile Lys Val Thr Ile Leu Glu Pro Met Ser Gly Glu Ser
                165                 170                 175

Leu Asp Ser Phe Thr Met Asp Leu Ser Glu Leu Asp Ile Gln Glu Lys
            180                 185                 190

Phe Leu Lys Thr Thr His Ser Ser His Ser Gly Gly Leu Val Ser Thr
        195                 200                 205

Met Val Lys Gly Thr Asp Asn Ser Asn Asp Ala Ile Lys Ser Ala Leu
    210                 215                 220

Asn Lys Ile Phe Ala Asn Ile Met Gln Glu Ile Asp Lys Lys Leu Thr
225                 230                 235                 240
```

Gln Lys Asn Leu Glu Ser Tyr Gln Lys Asp Ala Lys Glu Leu Lys Gly
                245                 250                 255

Lys Arg Asn Arg
        260

(2) INFORMATION FOR SEQ ID NO:3:

(i) SEQUENCE CHARACTERISTICS:
        (A) LENGTH: 1670 base pairs
        (B) TYPE: nucleic acid
        (C) STRANDEDNESS: double
        (D) TOPOLOGY: linear     (ii) MOLECULE TYPE: cDNA     (ix) FEATURE:
        (A) NAME/KEY: CDS
        (B) LOCATION: 793..1575

(ix) FEATURE:
        (A) NAME/KEY: mat_peptide
        (B) LOCATION: 793..1572

(xi) SEQUENCE DESCRIPTION: SEQ ID NO:3:

```
GATCCTATCG CGCCAAAGGT GGTATTAGGA ATAAGAGCTT GATTATTAAT CTCCCTGGTA      60

AGTCCAAAAA GTATTAGAGA ATGCTTAGAG GCGGTTTTTC CAGCGATTCC TTATTGCGTG     120

GATTTGATTT TAGGGAATTA CATGCAAGTG AATGAAAAAA ACATTCAAGC GTTTGCCCCC     180

AAACAATAAG GTAAAAAATG CCACTCACTC ATTTGAATGA AGAAAATCAA CCTAAAATGG     240

TGGATATAGG GGATAAAGAA ACCACTGAAA GAATCGCTCT AGCAAGCGGT CGTATCAGCA     300

TGAATAAAGA GGCTTATGAC GCTATTATCA ATCATGGCGT CAAAAAGGGT CCGGTATTAC     360

AAACTGCTAT TATTGCTGGG ATTATGGGGG CTAAAAAGAC AAGCGAACTC ATTCCCATGT     420

GCCATCCAAT CATGCTCAAT GGGGTGGATA TTGATATTTT AGAAGAAAAA GAGACTTGTA     480

GTTTTAAACT CTATGCGAGA GTCAAAACTC AAGCTAAAAC GGGCGTAGAA ATGGAAGCGC     540

TAATGAGTGT GAGCGTAGGG CTTTTAACCA TTTATGACAT GGTGAAAGCC ATTGATAAGA     600

GCATGACAAT TAGCGGTGTG ATGCTGGAAT ATAAAGTGG AGGCAAAAGT GGGGATTATA      660

ACGCTAAAAA ATAGAAAAAG ACTGATAATC TAAAGATATT AGGGTAAAAT AACATTTTGA     720

CAACAAAAGC GTGTTGGTTG CTTCGGATTT GTTGTTATAG AAGTCTAAAA TATTACAATC     780
```

AAGGATAGAA CG ATG AGA GCA AAT AAT CAT TTT AAA GAT TTT GCA TGG      828
          Met Arg Ala Asn Asn His Phe Lys Asp Phe Ala Trp
           1          5              10

AAA AAA TGC CTT TTA GGC GCG AGC GTG GTG GCT TTA TTA GTG GGA TGC      876
Lys Lys Cys Leu Leu Gly Ala Ser Val Val Ala Leu Leu Val Gly Cys
     15              20              25

AGC CCG CAT ATT ATT GAA ACC AAT GAA GTC GCT TTG AAA TTG AAT TAC      924
Ser Pro His Ile Ile Glu Thr Asn Glu Val Ala Leu Lys Leu Asn Tyr
   30              35              40

CAT CCA GCT AGC GAG AAA GTT CAA GCG TTA GAT GAA AAG ATT TTG CTT      972
His Pro Ala Ser Glu Lys Val Gln Ala Leu Asp Glu Lys Ile Leu Leu
45             50              55              60

TTA AGG CCA GCT TTC CAA TAT AGC GAT AAT ATC GCT AAA GAG TAT GAA     1020
Leu Arg Pro Ala Phe Gln Tyr Ser Asp Asn Ile Ala Lys Glu Tyr Glu
            65              70              75

AAC AAA TTC AAG AAT CAA ACC GCG CTC AAG GTT GAA CAG ATT TTG CAA     1068
Asn Lys Phe Lys Asn Gln Thr Ala Leu Lys Val Glu Gln Ile Leu Gln
        80              85              90

AAT CAA GGC TAT AAG GTT ATT AGC GTA GAT AGC AGC GAT AAA GAC GAT     1116

-continued

```
Asn Gln Gly Tyr Lys Val Ile Ser Val Asp Ser Ser Asp Lys Asp Asp
             95                 100                 105

TTT TCT TTT GCA CAA AAA AAA GAA GGG TAT TTG GCG GTT GCT ATG AAT        1164
Phe Ser Phe Ala Gln Lys Lys Glu Gly Tyr Leu Ala Val Ala Met Asn
        110                 115                 120

GGC GAA ATT GTT TTA CGC CCC GAT CCT AAA AGG ACC ATA CAG AAA AAA        1212
Gly Glu Ile Val Leu Arg Pro Asp Pro Lys Arg Thr Ile Gln Lys Lys
125                 130                 135                 140

TCA GAA CCC GGG TTA TTA TTC TCC ACC GGT TTG GAC AAA ATG GAA GGG        1260
Ser Glu Pro Gly Leu Leu Phe Ser Thr Gly Leu Asp Lys Met Glu Gly
                145                 150                 155

GTT TTA ATC CCG GCT GGG TTT ATT AAG GTT ACC ATA CTA GAG CCT ATG        1308
Val Leu Ile Pro Ala Gly Phe Ile Lys Val Thr Ile Leu Glu Pro Met
            160                 165                 170

AGT GGG GAA TCT TTG GAT TCT TTT ACG ATG GAT TTG AGC GAG TTG GAC        1356
Ser Gly Glu Ser Leu Asp Ser Phe Thr Met Asp Leu Ser Glu Leu Asp
        175                 180                 185

ATT CAA GAA AAA TTC TTA AAA ACC ACC CAT TCA AGC CAT AGC GGG GGG        1404
Ile Gln Glu Lys Phe Leu Lys Thr Thr His Ser Ser His Ser Gly Gly
    190                 195                 200

TTA GTT AGC ACT ATG GTT AAG GGA ACG GAT AAT TCT AAT GAC GCG ATC        1452
Leu Val Ser Thr Met Val Lys Gly Thr Asp Asn Ser Asn Asp Ala Ile
205                 210                 215                 220

AAG AGA GCT TTG AAT AAG ATT TTT GCA AAT ATC ATG CAA GAA ATA GAC        1500
Lys Arg Ala Leu Asn Lys Ile Phe Ala Asn Ile Met Gln Glu Ile Asp
                225                 230                 235

AAA AAA CTC ACT CAA AAG AAT TTA GAA TCT TAT CAA AAA GAC GCC AAA        1548
Lys Lys Leu Thr Gln Lys Asn Leu Glu Ser Tyr Gln Lys Asp Ala Lys
            240                 245                 250

GAA TTA AAA GGC AAA AGA AAC CGA TAA AAACAAATAA CGCATAAGAA              1595
Glu Leu Lys Gly Lys Arg Asn Arg  *
        255                 260

AAGAACGCTT GAATAAACTG CTTAAAAAGG GTTTTTTAGC GTTCTTTTTG AGCGTGTATT      1655

TAAGGGCTGA TGATC                                                       1670

(2) INFORMATION FOR SEQ ID NO:4:

(i) SEQUENCE CHARACTERISTICS:
        (A) LENGTH:  260 amino acids
        (B) TYPE:  amino acid
        (D) TOPOLOGY:  linear (ii) MOLECULE TYPE:  protein (xi) SEQUENCE DESCRIPTION: SEQ ID NO:4:

Met Arg Ala Asn Asn His Phe Lys Asp Phe Ala Trp Lys Lys Cys Leu
  1               5                  10                  15

Leu Gly Ala Ser Val Val Ala Leu Leu Val Gly Cys Ser Pro His Ile
             20                  25                  30

Ile Glu Thr Asn Glu Val Ala Leu Lys Leu Asn Tyr His Pro Ala Ser
         35                  40                  45

Glu Lys Val Gln Ala Leu Asp Glu Lys Ile Leu Leu Arg Pro Ala
     50                  55                  60

Phe Gln Tyr Ser Asp Asn Ile Ala Lys Glu Tyr Glu Asn Lys Phe Lys
 65                  70                  75                  80

Asn Gln Thr Ala Leu Lys Val Glu Gln Ile Leu Gln Asn Gln Gly Tyr
                 85                  90                  95

Lys Val Ile Ser Val Asp Ser Ser Asp Lys Asp Asp Phe Ser Phe Ala
            100                 105                 110
```

-continued

```
Gln Lys Lys Glu Gly Tyr Leu Ala Val Ala Met Asn Gly Glu Ile Val
        115                 120                 125

Leu Arg Pro Asp Pro Lys Arg Thr Ile Gln Lys Lys Ser Glu Pro Gly
    130                 135                 140

Leu Leu Phe Ser Thr Gly Leu Asp Lys Met Glu Gly Val Leu Ile Pro
145                 150                 155                 160

Ala Gly Phe Ile Lys Val Thr Ile Leu Glu Pro Met Ser Gly Glu Ser
            165                 170                 175

Leu Asp Ser Phe Thr Met Asp Leu Ser Glu Leu Asp Ile Gln Glu Lys
            180                 185                 190

Phe Leu Lys Thr Thr His Ser Ser His Ser Gly Gly Leu Val Ser Thr
        195                 200                 205

Met Val Lys Gly Thr Asp Asn Ser Asn Asp Ala Ile Lys Arg Ala Leu
    210                 215                 220

Asn Lys Ile Phe Ala Asn Ile Met Gln Glu Ile Asp Lys Lys Leu Thr
225                 230                 235                 240

Gln Lys Asn Leu Glu Ser Tyr Gln Lys Asp Ala Lys Glu Leu Lys Gly
            245                 250                 255

Lys Arg Asn Arg
            260
```

BACTERIAL ANTIGENS AND VACCINE COMPOSITIONS

TECHNICAL FIELD

The present invention provides recombinant polypeptides which constitute *Helicobacter pylori* antigens, said antigens being expressed on the surface of both dividing (bacillary) forms as well as resting (coccoid) forms of *H. pylori*, and giving rise to both systemic and local (mucosal) production of antibodies. The invention furthermore provides nucleic acid molecules coding for the said polypeptides, as well as vectors and host cells comprising such nucleic acid molecules. The said recombinant polypeptides are useful for the diagnosis of *H. pylori* infections and for the manufacture of vaccine compositions which will elicit a protective immune response against such infections, said vaccine compositions being suitable for both therapeutic and prophylactic use.

BACKGROUND ART

The gram-negative bacterium *Helicobacter pylori* is an important human pathogen, involved in several gastroduodenal diseases. Colonization of gastric epithelium by the bacterium leads to active inflammation and progressive chronic gastritis, with a greatly enhanced risk of progression to peptic ulcer disease.

In order to colonize the gastric mucosa, *H. pylori* uses a number of virulence factors. Such virulence factors comprise several adhesins, with which the bacterium associates with the mucus and/or binds to epithelial cells; ureases which helps to neutralize the acid environment; and proteolytic enzymes which makes the mucus more fluid.

Despite a strong apparent host immune response to *H. pylori*, with production of both local (mucosal) as well as systemic antibodies, the pathogen persists in the gastric mucosa, normally for the life of the host. The reason for this is probably that the spontaneously induced immune-response is inadequate or directed towards the wrong epitopes of the antigens.

In order to understand the pathogenesis and immunology of *H. pylori* infections, it is of great importance to define the antigenic structure of this bacterium. In particular, there is a need for characterization of surface-exposed like adhesins) and secreted proteins which, in many bacterial pathogens, have been shown to constitute the main virulence factors, and which can be useful for the diagnosis of *H. Pylori* and in the manufacture of vaccine compositions.

Cloning of the gene hpaA, which codes for a 20 kDa receptor-binding subunit of the N-acteylneuraminyllactose-binding fibrillar hemagglutinin (NLBH) of *H. pylori*, has been disclosed by Evans et al. (1993) J. Bacteriol. 175, 674–683.

Monoclonal antibodies (MAbs) against membrane preparations of *H. pylori* have been disclosed by Bölin et al. (1995) J. Clin. Microbiol. 33, 381–384. One of these MAbs, designated HP30-1:1:6, reacted with a 30 kDa protein which was shown to be exposed on the surface of intact bacteria and to have properties like that of an adhesin.

Whenever stressed or threatened, the *H. pylori* cell transforms from a bacillary to a coccoid form. In the coccoid form, the *H. pylori* cell is much less sensitive to antibiotics and other anti-bacterial agents. Circumstantial evidence indicate the *H. pylori* might be transmitted between individuals in this form, possibly via water or direct contact. An efficient vaccine composition should therefore elicit an immune response towards both the coccoid and the bacillary form of *H. pylori*. Since systemic immunity probably only plays a limited role in protection against mucosal infections, it is also important that the vaccine composition will enhance protective immune mechanisms locally in the stomach.

PURPOSE OF THE INVENTION

The purpose of this invention is to provide an antigenic *H. pylori* polypeptide which can be useful i.a. for eliciting a protective immune response against, and for diagnosis of, *H. pylori* infection. This purpose has been achieved by the recombinant cloning of a *H. pylori* gene which encodes a surface-exposed protein. The nucleic acid sequence of this gene is similar to the sequence of the hpaA gene as published by Evans et al. (1993) in the Journal of Bacteriology, vol. 175, 674–683. However, while the hpaA gene was reported to code for a 20 kDa protein, it has surprisingly been found that the DNA molecule according to the invention encodes a polypeptide with a molecular weight of 29 kDa.

The 29 kDa polypeptide is shown to be an antigenic protein which is expressed in all strains of *H. pylori*, also in coccoid forms of the bacterium, and which is able to induce a mucosal as well as a systemic immune-response in a host measured as antibody production. The 29 kDa polypeptide is expressed by all *H. pylori* strains tested and antibodies created towards this protein do not cross-react with common endogenous human bacteria of other species or with selected human tissues including the gastric mucosa. Thus being an essential, well conserved adhesin with immunogenic properties, the 29 kDa polypeptide will be useful both for the detection of *H. pylori* infections as well as for the manufacture of vaccine compositions, which when given in an appropriate pharmaceutical formulation will elicit a protective or therapeutic immune response against such infections.

The experimental data below thus indicates that the 29 kDa *H. pylori* protein is important for *H. pylori* colonization and/or persistence of infection, since binding of a monoclonal antibody for the 29 kDa protein results in complete inhibition of colonisation of *H. pylori* in mice. Furthermore, the 29 kDa *H. pylori* protein, when used as an oral immunogen, acts as a stimulator of an immune response leading to a significant reduction of colonisation of *H. pylori* in mice which were infected with *H. pylori* 1 month prior to immunization.

DISCLOSURE OF THE INVENTION

Throughout this description and in particular in the following examples, the terms "standard protocols" and "standard procedures", when used in the context of molecular cloning techniques, are to be understood as protocols and procedures found in an ordinary laboratory manual such as: Sambrook, J., Fritsch, E. F. and Maniatis, T. (1989) Molecular Cloning: A laboratory manual, 2nd Ed., Cold Spring Harbor Laboratory Press, Cold Spring Harbor, N.Y.

In a first important aspect, this invention provides a recombinant polypeptide which has an amino acid sequence identical with, or substantially similar to, a *Helicobacter pylori* surface-exposed antigen with an approximate molecular weight of 29 kDa.

The said surface-exposed antigen according to the invention has i.a. the following important properties:

It is an adhesin, which is important for the colonization of the gastric mucosa:

It is expressed on the surface of both dividing (bacillary) forms as well as resting (coccoid) forms of *H. pylori;*

It is a strong antigen giving rise to both systemic and local (mucosal) production of antibodies;

It is conserved in all tested strains of *H. pylori;*

Antibodies to the 29 kDa polypeptide do not cross-react with a number of different non-helicobacter bacteria, or with selected human tissues, including the gastric mucosa;

The 29 kDa polypeptide is lipidated and thus post-translationally modified. This feature of the polypeptide may be of importance for its immunogenicity and for its proper exposure on the surface of *H. pylori*. It is known in the art that lipid modification can be essential for the immunological properties of bacterial lipoproteins (see Weis, J. J. et al. (1994) Infection and Immunity, vol. 62, 4632–4636).

It is a putative virulence-factor, whereby the term "virulence factor" is to be understood a molecule specifically involved in adherence of *H. pylori* to the epithelial surface of the gastric mucosa and/or in the establishment and maintenance of *H. pylori* infection.

In a preferred form, the said polypeptide has an amino acid sequence according to positions 1–260, or 28–260, in SEQ ID NO: 2 or 4 of the Sequence Listing. As further described in the Experimental Section, it is believed that positions 1–260 in SEQ ID NO: 2 and 4 represent the uncleaved protein, while positions 1–27 represent a signal sequence and positions 28–260 represent the mature polypeptide. The only difference between SEQ ID NO: 2 and SEQ ID NO: 4 is that SEQ ID NO: 2 has a Ser residue in position 222, while SEQ ID NO: 4 has an Arg residue in the same position.

However, the polypeptide according to the invention is not to be limited strictly to a polypeptide with an amino acid sequence identical with the above mentioned positions in SEQ ID NO: 2 or 4 in the Sequence Listing. Rather the invention encompasses polypeptides carrying modifications like substitutions, small deletions, insertions or inversions, which polypeptides nevertheless have substantially the properties of the 29 kDa polypeptide according to the invention. Such properties include the ability to elicit a mucosal as well as systemic immune-response against *H. pylori* in a mammal host; the ability to work as an adhesin; and the presence of the polypeptide in both bacillary and coccoid forms of *H. pylori.*

Included in the invention are consequently polypeptides, the amino acid sequence of which is at least 90% homologous, preferably at least 95% homologous, with the amino acid sequence shown as positions 1–260, or positions 28–260, in SEQ ID NO: 2 or 4, in the Sequence Listing, which polypeptides nevertheless have substantially the biological activities of the 29 kDa polypeptide according to the invention.

Included in the invention are also peptides, with a length of at least 5 amino acids, which comprise an immunogenic epitope of the 29 kDa polypeptide according to the invention and retains the ability to elicit an immune response against *H. pylori* bacteria in a mammal host. Such epitope(s) can be presented alone or in the form of fusion proteins, where the epitope is fused to an inert or immunologically active carrier polypeptide. The identification of these epitopes will be based on the presence of host-generated antibodies towards different segments of the 29 kDa polypeptide.

One way of obtaining structural information on the epitopes of the 29 kDa polypeptide is the production and characterisation of monoclonal antibodies binding to the polypeptide, followed by mapping of epitopes by e.g. Pepscan analysis. Monoclonal antibodies can be produced by standard methods, such as those described by De St. Groth (1980) in J. Immunol. Methods, vol. 35, 1–21.

In another aspect, the invention provides an isolated and purified nucleic acid molecule which has a nucleotide sequence coding for a polypeptide as defined above. In a preferred form of the invention, the said nucleic acid molecule is a DNA molecule which has a nucleotide sequence identical with SEQ ID NO: 1 or 3 of the Sequence Listing. However, the DNA molecule according to the invention is not to be limited strictly to the sequence shown as SEQ ID NO: 1 or 3. Rather the invention encompasses DNA molecules carrying modifications like substitutions, small deletions, insertions or inversions, which nevertheless encode polypeptides having substantially the biochemical activity of the 29 kDa polypeptide according to the invention. It will be known to the skilled person that A←→G and T←→C substitutions, with no effect on the amino acid sequence, are not unusual in *H. pylori*. The only difference between SEQ ID NO: 1 and SEQ ID NO: 3 is that SEQ ID NO: 1 has a C residue in position 1458, while SEQ ID NO: 3 has an A residue in the same position.

Included in the invention are also DNA molecules which nucleotide sequences are degenerate, because of the genetic code, to the nucleotide sequence shown as SEQ ID NO: 1 or 3. Since there are 64 possible codons, but only 20 natural amino acids, most amino acids are coded for by more than one codon. This natural "degeneracy", or "redundancy", of the genetic code is well known m the art. It will thus be appreciated that the DNA sequence shown in the Sequence Listing is only an example within a large but definite group of DNA sequences which will encode the polypeptide as described above.

Consequently, the inventions includes an isolated nucleic acid molecule selected from:

(a) nucleic acid molecules comprising a nucleotide sequence which is identical with, or substantially similar to, positions 796–1572 or 874–1572 in SEQ ID NO: 1 or 3 in the Sequence Listing;

(b) nucleic acid molecules comprising a nucleotide sequence capable of hybridizing to a nucleotide sequence complementary the polypeptide coding region of a DNA molecule as defined in (a) and which codes for a polypeptide according to the invention, or a functionally equivalent modified form thereof; and (c) nucleic acid molecules comprising a nucleic acid sequence which is degenerate as a result of the genetic code to a nucleotide sequence as defined in (a) or (b) and which codes for a polypeptide according to the invention, or a functionally equivalent modified form thereof.

A further aspect of the invention is a vector which comprises the nucleic acid molecule according to the invention. Such a vector can preferably be the plasmid vector pAE1 (deposited May 16, 1995 under Accession No. NCIMB 40732 with The National Collections of Industrial and Marine Bacteria Limited, 23 St. Machar Drive, Aberdeen AB2 1RY, Scotland, UK) therefor.

A vector according to the invention can also be a replicable expression vector which carries and is capable of mediating the expression of a nucleic acid molecule according to the invention. In the present context the term "replicable" means that the vector is able to replicate in a given type of host cell into which is has been introduced. Examples of vectors are viruses such as bacteriophages, cosmids, plasmids and other recombination vectors. Nucleic acid molecules are inserted into vector genomes by standard methods known in the art. An expression vector according to the invention can preferably be any one of the vectors pAL30:1, pAL30:2, pAL30:3, pAL30:4 or, more preferably, pS863.

Included in the invention is also a host cell harbouring a vector according to the invention. Such a host cell can be a prokaryotic cell, a unicellular eukaryotic cell or a cell derived from a multicellular organism. The host cell can thus e.g. be a bacterial cell such as an *E. coli* cell; a cell from a yeast such as *Saccharomyces cervisiae* or *Pichia pastoris*, or a mammalian cell. The methods employed to effect introduction of the vector into the host cell are standard methods well known to a person familiar with recombinant DNA methods.

In another aspect, the invention provides a process for production of a polypeptide as defined above, said method comprising culturing a host cell transformed with an expression vector as defined above, under conditions whereby said polypeptide is produced, and recovering said polypeptide.

The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. The recombinant polypeptide expressed by the cells may be secreted, i.e. exported through the cell membrane, dependent on the type of cell and the composition of the vector.

If the polypeptide is produced intracellularly by the recombinant host, i.e. is not secreted by the cell, it may be recovered by standard procedures comprising cell disrupture by mechanical means, e.g. sonication or homogenization, or by enzymatic or chemical means followed by purification. In order to be secreted, the DNA sequence encoding the polypeptide should be preceded by a sequence coding for a signal peptide, the presence of which ensures secretion of the polypeptide from the cells so that at least a significant proportion of the polypeptide expressed is secreted into the culture medium and recovered.

A further aspect of the invention is a polypeptide according to the invention for use in therapy, for use in the diagnosis of *Helicobacter pylori* infection in a mammal, including man, and for use as a therapeutic or prophylactic vaccine.

Another important aspect of the invention is a vaccine composition for inducing a protective immune response in a mammal, including humans, against the bacillary and/or coccoid form of *Helicobacter pylori*. Such a vaccine composition comprises an immunogenically effective amount of a polypeptide as defined above, including at least a part of the 29 kDa polypeptide comprising an immunogenic epitope, or a modified form of said polypeptide which retains the capability to induce protective immunity against *Helicobacter pylori* infection. The term "modified form" includes, but is not restricted to, forms of the polypeptide which are post-translationally modified, e.g. lipidated. It is believed that the 29 kDa protein is lipidated, cf. Example 4 below.

The vaccine composition comprises optionally also a pharmaceutically acceptable carrier or diluent, or other immunologically active antigens for prophylactic or therapeutic use. Physiologically acceptable carriers and diluents are well known to those skilled in the art and include e.g. phosphate buffered saline (PBS), or, in the case of oral vaccines, $HCO_3^-$ based formulations or enterically coated powder formulations.

The vaccine composition can optionally include or be administered together with acid secretion inhibitors, preferably proton pump inhibitors (PPIs), e.g. omeprazole. The vaccine can be formulated in known delivery systems such as liposomes, ISCOMs, cochleates, etc. (see e.g. Rabinovich et al. (1994) Science 265, 1401–1404) or be attached to or included into polymer microspheres of degradable or non-degradable nature. The antigens could be associated with live attenuated bacteria, viruses or phages or with killed vectors of the same kind.

As will be demonstrated in the Experimental Section below, a vaccine composition according to the invention can be used for both therapeutic and prophylactic purposes. The vaccine composition according to the invention is preferably administered to any mammalian mucosa exemplified by the buccal, the nasal, the tonsillar, the gastric, the intestinal (small and large intestine), the rectal and the vaginal mucosa. The mucosal vaccines can be given together with for the purpose appropriate adjuvants. The vaccine can also be given parenterally, by subcutaneous, intracutaneous or intramuscular route, optionally together with the appropriate adjuvant.

An alternative approach for creating an immune response against the 29 kDa polypeptide is to use the approach known as "nucleic acid vaccination" or "naked DNA" vaccination. It is known in the art that injection into muscle of plasmid DNA encoding an antigen of interest can result in sustained expression of the antigen and generation of an immune response (see e.g. Rabinovich et al. supra). Several routes of administration are possible, such as parental, mucosal or via a "gene-gun" that delivers tiny amounts of DNA-coated gold beads (Fynan et al. (1993) Proc. Natl. Acad. Sci. U.S.A. 90, 11478–11482).

Thus, a nucleic acid molecule according to the invention can be expressed in plasmid comprising a suitable eukaryotic promoter. This "naked DNA" can then be injected intramuscularly or given intradermally via a "gene-gun". Epitopes of the expressed protein will be expressed by MHC molecules on the surface of the cells and trigger an immune response. Consequently, nucleic acid molecules and vectors as disclosed in the previous paragraphs for use in therapy, in particular for use as a vaccine, are further aspects of the invention. The use of such nucleic acid molecules and vectors in the manufacture of compositions for treatment, prophylaxis or diagnosis of *Helicobacter pylori* infection are also further aspects of the invention.

Yet another aspect of the invention is the use of a polypeptide as defined above, or a modified form of said polypeptide which retains the capability to induce protective immunity against *Helicobacter pylori* infection, in the manufacture of a compositions for the treatment, prophylaxis or diagnosis of *Helicobacter pylori* infection. Such compositions include in particular a vaccine composition eliciting a protective immune response against the bacillary and/or coccoid form of *Helicobacter pylori*. Included in the invention is also the said use in the manufacture of a diagnostic kit for diagnosis of *Helicobacter pylori* infection. Such a diagnostic kit is further described below.

In a further aspect, the invention provides a method of eliciting in a mammal, including man, a protective immune response against *Helicobacter pylori* infection, said method comprising the step of administering to the said mammal an immunologically effective amount of a vaccine composition as defined above. The term "immunologically effective amount" is intended to mean an amount which elicit a significant protective *Helicobacter pylori* response, which will eradicate a *H. pylori* infection in an infected mammal or prevent the infection in a susceptible mammal. Typically an immunologically effective amount would comprise approximately 1 μg to 100 mg, preferably approximately 10 μg to 10 mg, of *H. pylori* antigen for oral administration, or approximately less than 100 μg for parenteral administration.

Another aspect of the invention is a method of in vitro diagnosis of *Helicobacter pylori* infection, comprising at least one step wherein a polypeptide as defined above, including a part of the 29 kDa polypeptide which part comprises an immunogenic epitope, is used. The polypeptide can optionally be labelled and/or coupled to a solid support. A method of diagnosis can e.g. comprise the steps (a) contacting a said polypeptide, optionally bound to a solid support, with a body fluid taken from a mammal; and (b) detecting antibodies from the said body fluid binding to the said polypeptide. Preferred methods of detecting antibodies are ELISA (Enzyme linked immunoabsorbent assay) methods which are well known in the art.

In yet another aspect, the invention provides a diagnostic kit for the detection of *Helicobacter pylori* infection in a mammal, including man, comprising components which enable a diagnosis method as exemplified above to be carried out.

EXAMPLES

Example 1

Cloning and Expression of a 29 kDa Polypeptide from *H. pylori*

1.1. Bacterial Strains, Vectors and Growth Conditions

*H. pylori* CCUG 17874 (=NTCC 11637) was grown on horse blood agar plates in an microaerophilic atmosphere. *E. coli* strains XL1-Blue MRF' and XLOLR (Stratagene, La Jolla, Calif.) were used as host strains for cloning experiments and were grown in Luria-Bertani broth (LB) or NZY medium supplemented with 0.2% maltose and 10 mM $MgSO_4$ when used for lambda infection. The lambda expression vector ZAP Express™ and its phagemid derivative pBK-CMV were obtained from Stratagene.

1.2. DNA Techniques

Chromosomal DNA from *H. pylori* 17874 was prepared by suspending bacteria from plates incubated for 48 h in 50 mM Tris-Cl, pH 8.0, 25% sucrose, 50 mM EDTA containing 10 mg/ml lysozyme, and 5 ng/ml DNase-free RNase (Boehringer Mannheim Scandinavia AB, Bromma, Sweden). The suspension was incubated for 10 min at +37° C. An equal volume of lysis buffer (0.4% Triton X100 in 50 mM Tris-Cl, pH 8.0; and 62.5 mM EDTA) was added and the suspension was incubated at room temperature until a noticeable lysis of the bacteria occurred. The suspension was then extracted in three steps, with buffered phenol (pH 8.0), phenol/chloroform and chloroform, respectively. The DNA was precipitated from the aqueous phase and dissolved in TE-buffer (10 mM Tris-Cl, pH 8.0; and 1 mM EDTA).

Restriction enzymes were purchased from Boehringer Mannheim Scandinavia AB and used according to the manufacturers instructions. Plasmids and lambda DNA were purified with Wizard kits (Promega, Madison, Wis.). Sequencing was performed using the Sequenase 2.0 kit (Amersham Sweden AB, Solna, Sweden). Oligonucleotides were purchased from Innovagen, Lund, Sweden. PCR was performed using Taq DNA polymerase (Boehringer-Mannheim Scandinavia AB).

1.3. Construction of a *H. pylori* Genomic Library

Chromosomal DNA fragments in the size range 2–12 kb were purified from partially Sau3A-cleaved *H. pylori* 17874 DNA and cloned into BamHI digested ZAP Express™ vector as described in the Stratagene protocol. Following in vitro packaging, the library was titrated by infecting strain XL-1 Blue MRF and plated onto indicator plates containing isopropyl-β-D-thiogalactopyranoside (IPTG) and 5-bromo-4-chloro-3-indolyl-β-D-galactopyranosid (X-Gal). The titer of the library was $1.2 \times 10^6$ PFU/ml with 85% recombinants.

Plaques expressing the 29 kDa polypeptide were detected by immunological screening using MAb HP30-1:1:6 (Bölin et al. (1995) J. Clin. Microbiol. 33, 381–384) according to standard methods. Positive plaques were isolated and the plating and screening with the MAb was repeated until plaque purity was obtained. The conversion to the phagemid form of the ZAP Express clones was accomplished using the ExAssist protocol (Stratagene).

1.4. Immunoblotting and Dot Blot Test

Figure 1:
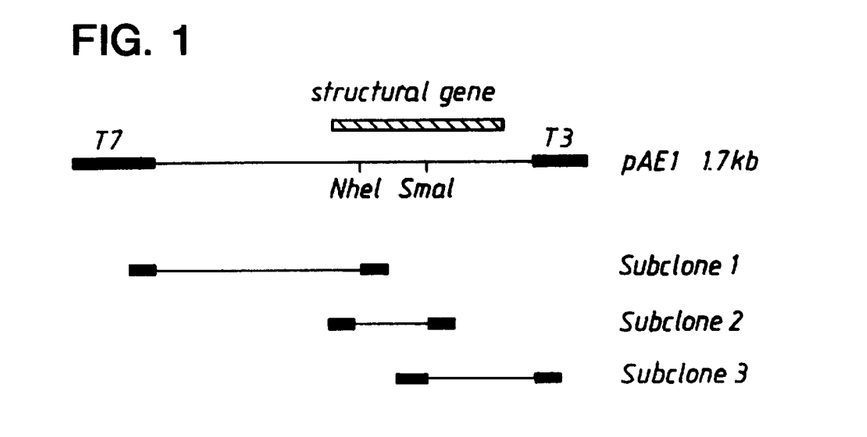
FIG. 1: Restriction enzyme map of plasmid pAE1 containing the 1.7 kb fragment of *H. pylori* encoding the 29 kDa polypeptide. Hatched bar indicates the position of the structural gene. The location of the T3 and T7 promoter sequences are shown above the black bars indicating the vector.
Figure 2A:
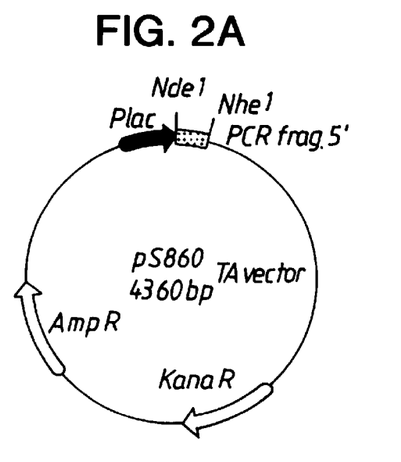
FIG. 2: Plasmid maps of pS860, pS861, pS862 and pS863. Filled arrows: lac operon promoter (Plac) or bacteriophage T7 RNA Polymerase promoter (T7promoter). Grey fill: PCR generated 5'-end or 3'-end of the 29 kDa gene. Terminator: T7 transcription terminator. Ori: pBR322 plasmid replication origin.
Figure 2B:
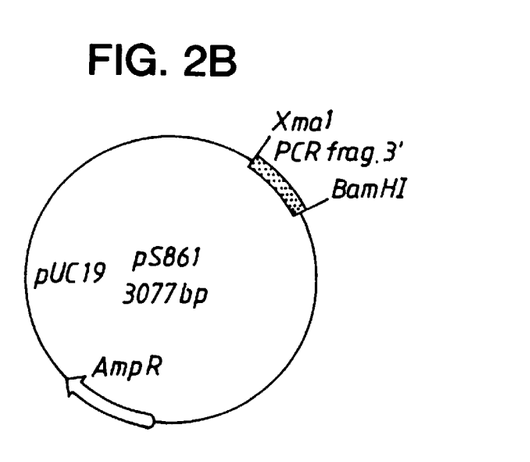
Figure 2C:
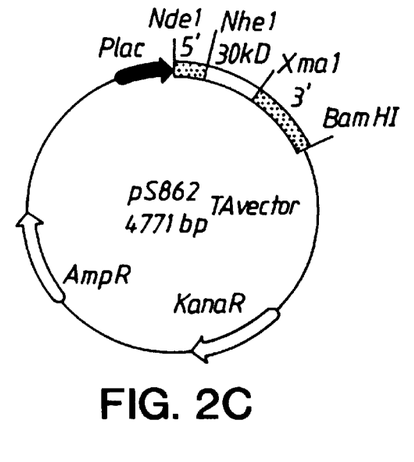
Figure 2D:
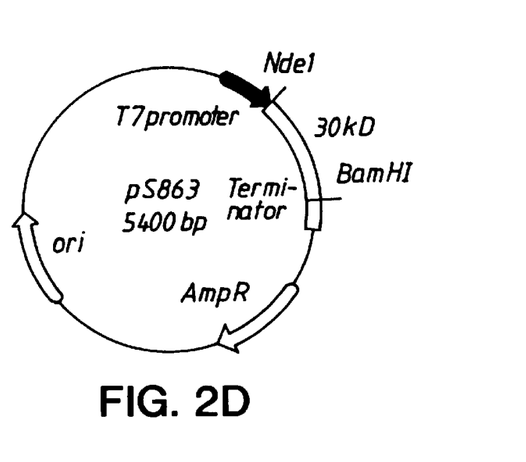

Overnight cultures of *E. coli* XLOLR containing plasmids with cloned inserts from *H. pylori* 17874 depicted in FIG. 1, were diluted 1:100 in 5 ml of LB medium with 50 mg/ml kanamycin. The cultures were incubated at +37° C. until the OD at 600 nm was 0.7. IPTG was added to a final concentration of 1 mM and the bacteria were grown for additional 2 h.

Cultures without IPTG were grown similarly. The cultures were centrifuged and resuspended in 1/10 of the volume. Ten μl of the suspension were mixed with an equal volume of 2× sample buffer, boiled and analysed by SDS-PAGE. Strain XLOLR, grown in the same way but without kanamycin, served as a negative control. A suspension of *H. pylori* 17874 in PBS (OD at 600 nm=1.0) was used as a positive control.

After immobilization of the protein profiles on nitrocellulose sheets, reaction with the 29 kDa polypeptide-specific MAb HP30-1:1:6 diluted 1:10 was carried out as described previously (Bölin et al., 1995) and bound antibodies were detected by using anti-mouse IgG labelled with peroxidase. Filters were developed with hydrogen peroxide substrate and 4-chloronaphtol chromogen (BioRad Svenska AB).

The dot blot test was performed using overnight cultures of the above strains. Two μl of a suspension were spotted on nitrocellulose filters, air-dried and incubated with MAb HP30-1:1:6 diluted 1:10 for one h. Subsequent steps were carried out as described for immunoblotting.

1.5. Molecular Cloning

Partially digested chromosomal DNA from *H. pylori* strain 17874 were cloned into a lambda expression vector (ZAP Express™). Four plaques expressing the 29 kDa polypeptide were detected after screening of 24 000 plaques for reaction with the 29 kDa polypeptide-specific MAb. The positive plaques were purified and the size of the cloned inserts were examined by digestion of DNA-preparations with XbaI and SalI. The inserts were from 3.7 to 1.78 kb in size. After in vivo excision of the pBK-CMV phagemids from the four positive plaques, restriction enzyme maps were constructed and compared with the inserts in the lambda vector. The phagemids were found to contain overlapping DNA-fragments with the same size as in the lambda vector. Most of the restriction enzymes tested, except for SmaI and NheI, did not cleave the cloned fragments.

The restriction map of the smallest cloned 1.7 fragment (pAE1) that were further analyzed is shown in FIG. 1. One of the cloned inserts were in the opposite direction with regard to the vector promoter. When whole cell extracts of the E. coli strains containing these plasmids were analysed in immunoblotting with MAb HP30-1:1:6, they were all found to express a polypeptide with the same molecular weight as H. pylori 17874. No difference in expression of the 29 kDa polypeptide was seen when the vector promoter was induced with IPTG. This indicated that the gene was transcribed from its own promoter. Three subclones containing the DNA fragments indicated in FIG. 1 were constructed and examined for expression of the 29 kDa polypeptide. None of the clones expressed the polypeptide. When XLOLR (pAE1) were tested in the dot blot assay (Bölin et al., 1995) and compared with H. pylori, it was found to be weakly positive indicating that some of the expressed polypeptide may be exposed on the surface.

1.6. Analysis of the DNA Sequence

Both strands of the 1.7 kb insert of pAE1 and the subclones were sequenced using T3- and T7-specific primers and, when necessary, supplemented with specific primers to cover regions of the sequence not available with the standard primers. The computer analysis showed that the sequence (SEQ ID NO: 1) contained an open reading frame (ORF) of 780 bp on one strand, spanning the restriction enzyme sites used for subcloning (FIG. 1). A putative ribosome binding site could be identified (positions 782–785 of SEQ ID NO: 1). The ORF coded for 260 amino acids of a polypeptide of a molecular weight of 29,126 Da (SEQ ID NO: 2).

The amino acid sequence was found to contain a possible signal sequence of 27 amino acids. The sequence Leu-Val-Gly-Cys (positions 25 to 28 in SEQ ID NO: 2 and 4) is one of the consensus sequences (Leu-X-Y-Cys) assigned as a recognition site for the enzyme signal peptidase II. The signal peptidase II cleaves the signal sequences before the cysteine residue in prolipoproteins. The characteristics of the signal sequence thus suggest that the 29 kDa protein is a lipoprotein and that the mature protein comprises amino adds 28 to 260.

1.7. Expression of the Recombinant 29 kDa Polypeptide in E. coli

The recombinant 29 kDa polypeptide was produced in high concentration in E. coli N4830-1 from the expression vector construct pAL30, which contains the entire gene of the 29 kDa polypeptide (positions 771–1667 in SEQ ID NO: 1 and 3) The vector used for the construct was pML-LCTB λ7 (obtained from Michael Lebens, University of Gothenburg, Sweden) which contains a strong $\lambda P_L$ promoter. The vector also comprises a β-lactamase gene giving ampicillin resistance. The LCTB gene (encoding the cholera toxin and its signal peptide), which is inserted between the $\lambda P_L$ promoter and a terminator region in the vector, was excised from the vector by cleaving with the restriction enzymes SmaI and HindIII.

The structural gene encoding the 29 kDa polypeptide, including its signal sequence, was amplified by Polymerase Chain Reaction (PCR). The primers used were HP30N (GGC GTA GAA ATG GAA GCG C; corresponding to positions 522 to 540 in SEQ ID NO: 1 and 3) which binds 271 bp upstream of the ATG start codon and HP30C (CCC AAG ATT CAT CAG CCC TTA AAT ACA CG) which recognizes a DNA fragment 855 bp downstream the start codon (corresponding to positions 1648 to 1667 in SEQ ID NO: 1 and 3). The HP30C primer contained a HindIII cleavage site which by the PCR reaction was added to the sequence of the 29 kDa polypeptide gene. The resulting PCR product was 1.1 kb. This DNA fragment was cleaved by SspI and HindIII which gave a fragment of 0.9 kb which was ligated to the vector fragment (2.7 kb). The vector construct now called pAL30 (3.6 kb) was transformed into E. coli N4830-1 by electroporation. Four positive clones were found (pAL30:1, 2, 3, 4).

To induce expression of the recombinant polypeptide the N4830-1 cells containing the pAL30: 1 to 4 were grown over night at +30° C. (the lambda cI repressor inhibits the transcription at this temperature) in 1×LB with ampicillin (100 μg/ml). A small part of this over night culture was inoculated in 5 ml 1×LB with ampicillin and the cells were grown at +30° C. until the O.D. at 600 nm was about 0.7. The temperature was then raised to +42° C., whereby the repressor was inactivated, and incubated for two additional hours.

Samples taken before and after induction was analysed on 14% SDS-PAGE and by immunoblotting, using the monoclonal antibody HP30-1:1:6 which is specific for the 29 kDa polypeptide. All three induced clones used in immunoblotting (pAL30: 1, 3 and 4) expressed a large amount of the recombinant polypeptide after induction. The suspension from the non-induced cells contained only a low amount of the 29 kDa polypeptide.

The clone pAL30:1 was chosen for further analysis. In order to verify that the clone really contained the gene encoding the 29 kDa polypeptide, the ends of the fragment inserted in the vector was sequenced. It was verified that the sequence inserted into the expression vector corresponded to the expected sequence of the cloned PCR fragment.

Example 2

Kinetics of Expression of the 29 kDa Polypeptide During Various Culture Conditions Two strains of H. pylori were used, namely CCUG 17874 (a laboratory strain) and Hel 73 (recently isolated from a patient suffering from duodenal ulcer). Cultivation was performed on blood agar plates, as well as in Brucella Broth supplemented with cyclodextrin. All cultures were incubated in a microaerophilic atmosphere consisting of 5% $O_2$, 10% $CO_2$ and 85% $N_2$. Bacteria were harvested after 2, 4 and 7 days, washed once in PBS and kept at −20° C. for subsequent analysis. The expression of the 29 kDa surface polypeptide was analysed by inhibition-ELISA employing specific monoclonal antibodies as previously used for detection of E. coli surface antigens (Lopez-Vidal, Y and Svennerholm, A-M., J. Clin. Microbiol. 28, 1906–) against the polypeptide. These antibodies were also used in immunoelectron microscopy.

When CCUG 17874 had been cultivated for 7 days, on blood agar plates as well as in brucella broth, approximately 70% of the bacteria had converted from the spiral form to the coccoid form. This conversion occurred already after 3 days in Hel 73. The inhibition-ELISA showed a fairly constant concentration of the 29 kDa polypeptide in samples from both plate and broth cultures, during the 7 days. The presence of the polypeptide was confirmed by immunoelectron microscopy. The 29 kDa polypeptide was found to be well preserved in coccoid forms of *H. pylori*. The 29 kDa polypeptide was found to be more abundant in Hel 73 than in CCUG 17874.

Example 3

Antibody Responses Against the 29 kDa Polypeptide

Antibody responses against the 29 kDa polypeptide were determined in sera and gastric aspirates from patients with duodenal ulcers (n=19), in asymptotic *H. pylori* carriers (n=18) and in non-infected age-matched controls (n=20).

Antibody levels against the 29 kDa polypeptide were tested in gastric aspirates and in sera from the three groups of subjects, by means of different ELISA methods. A majority of the infected subjects had significantly higher levels, compared with the healthy control persons, of specific antibodies against the 29 kDa polypeptide both in serum and in gastric aspirates. Antibody titers in asymptotic carriers were comparable to those of the symptomatic patients.

Example 4

Labelling of Polypeptides with [$^3$H]Palmitate

Since the amino add sequence of the 29 kDa polypeptide contained a possible signal peptide typical for lipoproteins, the labelling of the protein with radioactive palmitic acid was investigated:

*E. coli* N4830-1, either lacking or carrying pAL30:1, were grown at +30° C. in LB-broth supplemented with 50 μg of carbencillin/ml. At a cell density of $10^8$ bacteria/ml, [$^3$H] palmitic acid (5 mCi/ml; DuPont NEN, Boston, Mass.) was added to a final concentration of 50 μCi/ml. The temperature was raised to +42° C. and the cultures were incubated for another 12 h. The cells were collected by centrifugation and lysed in SDS-PAGE lysis buffer. After electrophoresis, the gel was processed for flougraphy by immersing the gel in Amplify™ (Amersham International, UK) for 30 min, drying it between cellophane sheets and exposing the gel to X-ray film at −70° C. for 36 h.

The results indicated that the 29 kDa polypeptide is lipidated and thus post-translationally modified.

Example 5

Triton X-114 Partitioning of *E. coli* Expressing the Recombinant 29 kDa Polypeptide

*E. coli* cells carrying pAL30:1 were grown at +30° C. in LB-broth supplemented with 50 pg carbencillin/ml. At a cell density of $10^8$ bacteria/ml, the temperature was raised to +42° C. and the cultures were incubated for another 3 h. The cells were collected by centrifugation (11.300×g, 10 min, +4° C.) and resuspended in 25 ml of PBS per gram of cell pellet. The suspension was frozen and then thawed at room temperature, and 25 μl DNAse I (10 μg/μl) was added. The sample was gently shaken by inversion for 30 min at room temperature and chilled to 8–12° C. followed by the addition of Triton X-114 (final concentration 0.3%). After incubation by gentle inversion at +4° C. for 3 h the insoluble material was collected by centrifugation (18.900×x g, 10 min, +25° C.).

The phases were analysed by SDS-PAGE and the identity of the 29 kDa polypeptide was verified by Western blotting using MAb HP30-1:1:6. The results indicated that the 29 kDa polypeptide appeared in the detergent phase, which confirmed that it is a lipoprotein. It is known in the art that integral membrane proteins are normally recovered in the detergent phase (Bordier, C. (1981) J. Biol. Chem., vol. 256, 1604–1607).

This experiment also verified that a plasmid inserted into *E. coli* could express and produce the 29 kDa protein. This is important for the future production of a vaccine in larger scale, since *H. pylori* does not grow very well or fast.

Example 6

Construction of Expression Vector pS863 for Production of High Levels of *H. pylori* 29 kDa Protein 6.1. Preparation of pS860

To generate convenient restriction sites for the 5'-end of the 29 kDa gene, two synthetic oligonucleotides for PCR amplification were synthesized. The plasmid pS852 (identical to the plasmid pAL30:1 described in Example 1.7) was used as a template for the PCR amplification. The sequences of these two oligonucleotides are listed below:

```
       EcoRI   NdeI
5'-CGGAATTCCATATGAGAGCAAATAATCATTTTAAAG-3'

BamHI  XmaI   NheI
5'-GCGGATCCCCCGGGGCTAGCTGGATGGTAATTCAATTTC-3'
```

PCR amplification was performed and the 169 bp amplified fragment was ligated into the TA vector (Mead, D. A. et al. (1991) Bio/Technology 9, 657–663). The constructed plasmid was designated pS860 (FIG. 2). The sequence of the construct was confirmed by dideoxy sequencing (Sanger et al. (1977) Proc. Natl. Acad. Sci. U.S.A. 74, 5463–5467).

6.2. Preparation of pS861

In order to change restriction sites in the 3'-end of the 29 kDa gene two synthetic oligonucleotides for PCR amplification were synthesized. The plasmid pS852 (pAL30:1) was used as a template for the PCR amplification. The sequences of the two oligonucleotides are listed below:

```
      EcoRI   XmaI
5'-CGGAATTCCCCGGGTTATTATTCTCCACCGG-3'

PstI      BamHI
5'-CGCTGCAGGGATCCTTATTATCGGTTTCTTTTGCCTTTTAA-3'
```

PCR amplification were performed and the amplified fragment was digested with XmaI and BamHI generating a 357 bp fragment This fragment was cloned into pUC19, the constructed plasmid was designated pS861 (FIG. 2). The sequence of the construct was confirmed by dideoxy sequencing (Sanger et al. (1977) Proc. Natl. Acad. Sci. U.S.A. 74, 5463–5467).

6.3. Preparation of Plasmid pS862

The cDNA encoding the middle part of the 29 kDa gene was isolated by gel electrophoresis as a 280 bp NheI/XmaI fragment from the plasmid pS852 (pAL30:1). This fragment was ligated together with a 357 bp XmaI/BamHI fragment from pS861 and a 4061 bp NheI/BamHI fragment from pS861. The generated plasmid was designated pS862 (FIG. 2).

6.4. Preparation of Plasmid pS863

Thereafter, a 795 bp NdeI and BamHI restriction fragment was isolated from pS862 and ligated to a 4 kb NdeI/BamHI fragment from T7 vector pS637(pET-3a) (Studier, F. W. et al. (1990) Methods Enzymol. 185, 60–89). The resulting expression vector was designated pS863 (FIG. 2).

Example 7

Purification of Recombinant H. pylori 29 kDa Lipoprotein 7.1. Host Strains and Bacterial Cultures The expression vector pS863 was transformed into the following E. coli host strains; BL21(DE3); BL21(DE3) pLysS; and BL21(DE3)pLysE. The expression experiments were carried out essentially as described by Studier et al. (Methods Enzymol. 185, 60–89, 1990). The bacteria were grown in LB medium (Ausubel, F. M. et al. (eds.) Current Protocols in Molecular Biology, John Wiley & Sons, New York, 1992) containing 50 µg/ml carbencillin In addition, when BL21(DE3)pLysS and BL21(DE3)pLysE were used, the medium was supplemented with 30 µg/ml chloramphenicol. For induction of the T7 expression system, the cultures were grown to a density of approximately $OD_{600}$=0.5, and then supplemented with 0.4 mM IPTG for induction. The cells were harvested about 180 minutes after induction. The host strain that gave the highest expression level was BL21 (DE3)pLysS.

7.2. Purification of the H. pylori 29 kDa Lipoprotein

Cultures of E. coli BL21(DE3)/pLysS transformed with plasmid pS863 were grown as described above and the cells were collected by centrifugation and resuspended in cold buffer (50 mM Tris-HCl, 2 mM EDTA, 10 mM NaCl, pH 8.0). For each gram of pellet (wet weight) 35 ml of buffer was added.

7.2.1. Triton X-114 Extraction

To extract the lipoprotein, Triton X-114 (TX-114) was added to a final concentration of 1.5% (v/v) and the suspension was stirred for one hour at 0° C. The Triton-insoluble material was pelleted by centrifugation at 18,900×g for 10 min. In some cases was the pellet extracted once more but with half the volume of TX-114 containing buffer. After the second TX-114 extraction the pellet was discarded.

Phase partitioning of the supernatant from the TX-114 extraction was obtained by incubating it for 15 min at +30° C. with occasional mixing. The turbid solution was centrifuged at 31,300×g for 30 min at +30° C. The lower detergent phase was collected and diluted to 1% TX-114 with cold buffer (50 mM Tris-HCl, 2 mM EDTA, 10 mM NaCl, pH 8.0).

7.2.2. Q-sepharose, pH 8.0

The diluted TX-114-phase was applied to a Q-sepharose column (Pharmacia) (20 ml/3 g cell pellet) equilibrated with buffer (50 mM Tris-HCl, 2 mM EDTA, 10 mM NaCl, 0.1% Triton X-100, pH 8.0). The 29 kDa lipoprotein was collected as the non-binding fraction. This fraction was phase partitioned by incubating it at +30° C. with occasional mixing until the solution was turbid. The two phases were separated by centrifugation at 31,300×g for 30 min at +30° C. The lower detergent phase was collected and diluted to 1% TX-114 with cold buffer (10 mM Tris-HCl, 2 mM EDTA, pH 8.6).

7.23. Q-sepharose, pH 8.6

The diluted TX-114-phase was applied to a 100 ml Q-sepharose column (Pharmacia) equilibrated with buffer (10 mM Tris-HCl, 2 mM EDTA, pH 8.6). The non-binding fraction contained TX-114. The column was washed with buffer A (10 mM Tris-HCl, 2 mM EDTA, 0.1% Triton X-100, pH 8.6). The 29 kDa lipoprotein was collected by a salt gradient with buffer B (10 mM Tris-HCl, 2 mM EDTA, 0.1% Triton X-100, 1M NaCl, pH 8.6). The gradient was as follows; 0–50% B, 40 ml; 50–100% B, 100 ml. The 29 kDa lipoprotein eluted between 60–70% B.

7.2.4. SDS-PAGE and Protein Electroblotting

Protein samples from the different purification steps were solubilized in sample buffer (50 mM Tris-HCl, pH 6.8, 8% glycerol, 1.6% SDS, 4% β-mercaptoethanol, 0.02% bromphenol blue) and separated on Novex precast gradient gels (4–20% polyacrylamide) or BioRad precast gradient gels (10–20% polyacrylamide). The electrophoresis running buffer contained 25 mM Tris, 192 mM glycin, 0.5% SDS, pH 8.3. Gels were stained with 0.1% Coomassie Brilliant Blue R-250 in 40% methanol, 10% acetic add and destained with 10% methanol, 10% acetic acid.

Gels intended for Semi-Dry-electroblotting were not stained but soaked in Transfer buffer (48 mM Tris, 38 mM glycin, 0.075% SDS, 20% MeOH) and proteins were transferred onto PVDF membranes (Immobilon®, Millipore, U.S.A.) by a SemiDry electroblotting apparatus (BioRad). Immunodetection was accomplished by first blocking the PVDF membrane for one hour in 2% BSA in TBS (50 mM Tris-HCl, 2.5M NaCl, pH 8.2) and thereafter the membrane was incubated for one hour with a specific monoclonal antibody (IgG1) against the 29 kDa lipoprotein diluted 1:10 with 1% BSA in TBS. After a washing step with TBS the membrane was incubated for one hour with an alkaline phosphatase-conjugated anti-mouse IgG antibody (Dakopatts, Denmark). After an additional wash the membrane was developed with appropriate substrates (5-bromo-4-chloro-3-indolyl phosphate (BCIP) and nitroblue tetrazolium (NBT) (Sigma)).

7.2.5. Protein Concentration and Pyrogenicity

Total protein concentration was determined by the bicinchoninic acid method (BCA Protein Assay. Pierce Chemical Company, U.S.A.).

The endotoxin content was assayed by a chromogenic Limulus amebocyte lysate (LAL) test (LAL COAMATIC® Endotoxin. Endosafe Inc. U.S.A.)

Stained SDS-gels were scanned (BioRad Imager GS-) to determine the relative amount of protein contaminants in the final preparations. The preparations contained <10% protein contaminants.

Example 8

Analysis of the H. pylori 29 kDa Protein for Use as a Vaccine 8.1. Materials & Methods 8.1.1. Animals Female SPF BALB/c mice were purchased from Bomholt Breeding centre (Denmark). They were kept in ordinary makrolon cages with free supply of water and food. The animals were 4–6 weeks old at arrival.

8.1.2. Infection

After a minimum of one week of acclimatization, the animals were infected with a type 2 strain of H. pylori (strain 244, originally isolated from an ulcer patient). This strain has earlier proven to be a good colonizer of the mouse stomach. The bacteria were grown overnight in Brucella broth supplemented with 10% fetal calf serum, at +37° C. in a microaerophilic atmosphere (10% $CO_2$, 5% $O_2$). The animals were given an oral dose of omeprazole (400 mmol/kg) and after 3–5 h an oral inoculation of H. pylori (approximately $10^8$ cfu/animal). Infection was checked in control animals 2–3 weeks after the inoculation.

8.1.3. Immunizations

The animals were immunized 4 times over a 34 day period (day 1, 15, 25 and 35). Purified antigen was given at a dose of 100 µg/mouse and membrane proteins (MP) at a dose of 0.5 mg/dose. Membrane proteins were prepared by sonication of bacteria in PBS. Debris was removed by spinning the sonicate at +4° C., 2000 rpm for 5 min. The supernatant was transferred to a new tube and spun at +4° C., 15,000 rpm for 20 min. The pellet was recovered and stored at −70° C. until use.

As an adjuvant, the animals were also given 10 μg/mouse of cholera toxin (CT) with each immunization. Omeprazole (400 μmol/kg) was given orally to the animals 3–5 h prior to immunization as a way of protecting the antigens from acid degradation. Animals were sacrificed 4 weeks after final immunization.

8.1.4. Passive Protection

To analyze the effect of monoclonal antibodies (MAbs) on the ability of *H. pylori* to colonize the mouse stomach, MAbs with different specificities were mixed with *H. pylori* 10 min prior to inoculation as described above. MAbs raised against the 29 kDa protein (HP30-1:1:6), against urease (Ure 8:1); and against the *E. coli* heat-stable protein (ST 1:3) were used. The MAbs were titrated in an ELISA to allow for equal amounts of each MAb to be used in the experiment. A number of $10^7$ bacteria per mouse were used for inoculation. The mice were sacrificed 2 weeks post inoculation.

8.1.5. Analysis of Infection

The mice were sacrificed by $CO_2$ and cervical dislocation. The abdomen was opened and the stomach removed. After cutting the stomach along the greater curvature, it was rinsed in saline. The mucosa from the antrum and corpus of an area of 25 $mm^2$ was scraped separately with a surgical scalpel. The mucosa scraping was suspended in Brucella broth and plated onto Blood Skirrow plates. The plates were incubated under microaerophilic conditions for 3–5 days and the number of colonies was counted. The identity of *H. pylori* was ascertained by urease and catalase test and by direct microscopy or Gram staining.

8.2. Results

8.2.1 Passive Protection

Figure 3:
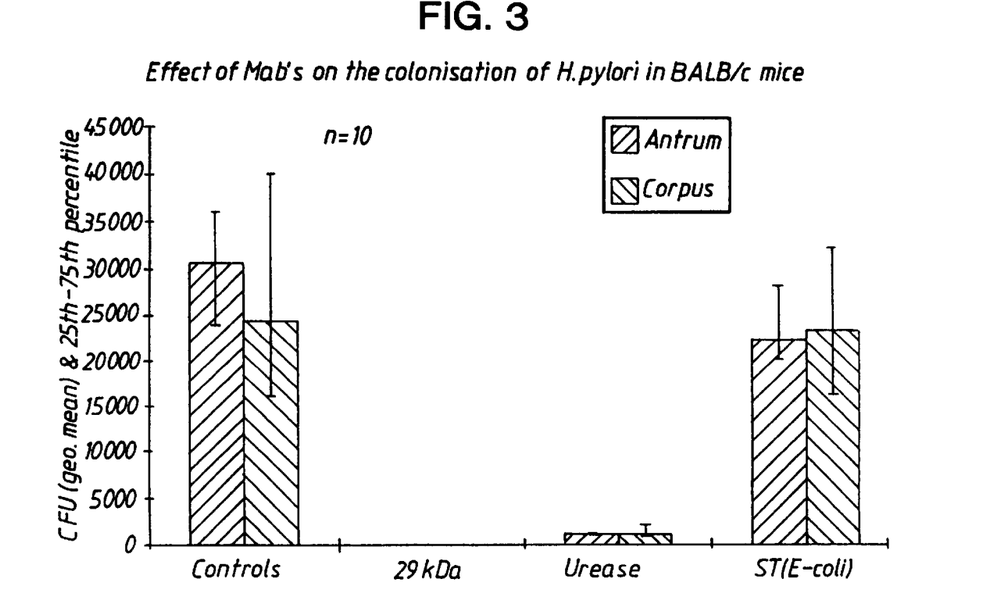
FIG. 3: Effect of monoclonal antibodies on the colonisation of *H. pylori* in BALB/c mice.

Three groups with 10 animals in each were given a mixture of *H. pylori* strain 244 and a MAb, and one group was given only *H. pylori*. The mixture of MAb and bacteria was allowed to react for 10 min before being inoculated into the mice. None of the MAbs used had any dear effect on the bacteria in vitro. Two weeks after inoculation, the mice were sacrificed and the infection rate was determined for each group (FIG. 3). All of the mice in the control group and those inoculated with the ST Mab were infected. In the urease MAb group all mice were infected, but to a significantly lower degree compared with the controls. In the group inoculated with the MAb against the 29 kDa protein, none of the mice were infected.

8.2.2. Therapeutic Immunization

Figure 4:
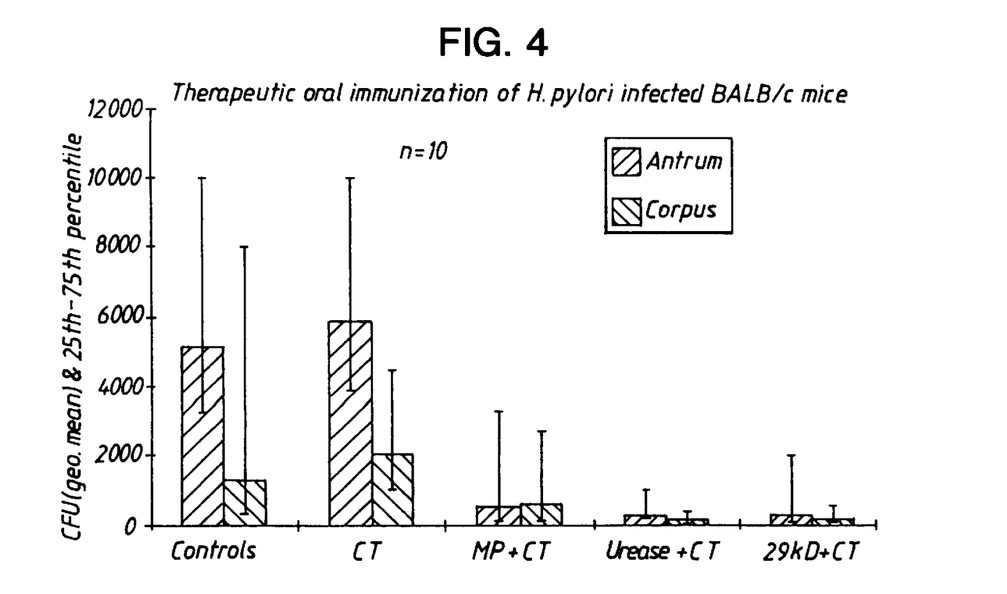
FIG. 4: Therapeutic oral immunization of *H. pylori* infected BALB/c mice.

The animals in this study were infected with *H. pylori* strain 244 one month prior to immunizations. Mice in groups of ten were then immunized with either cholera toxin (CT) or CT together with membrane proteins, urease or the 29 kDa protein. Control animals received vehicle only (PBS). One month after the final immunization, the animals were sacrificed and CFU was determined (FIG. 4). All control animals, as well as those immunized with only CT, were infected. Animals actively immunized with urease and CT, or with 29 kDa protein and CT, had significantly decreased CFU values compared with the controls. Only one animal in the urease-immunized group was completely cured from the infection.

8.3. Conclusions

The results above indicate that the 29 kDa *H. pylori* protein is important for the colonization and/or persistence of an infection, since binding of a MAb to this structure result in complete inhibition of colonisation.

Furthermore, the 29 kDa *H. pylori* protein, when used as an oral immunogen in conjunction with cholera toxin as an oral adjuvant, acts as a stimulator of an immune response leading to a significant reduction of the degree of colonisation of *H. pylori* in the used animal model.

Taken together, these results strongly support the use of the 29 kDa *H. pylori* protein in an oral vaccine formulation for the use in humans to treat and prevent *H. pylori* infections.

DEPOSIT OF MICROORGANISMS

The plasmid pAE1 has been deposited under the Budapest Treaty at the National Collections of Industrial and Marine Bacteria (NCIMB), Aberdeen, Scotland, UK, and under accession number NCIMB 40732. The date of deposit is May 16, 1995.

---

We claim:

1. An isolated nucleic acid segment which comprises a nucleotide sequence coding for a polypeptide selected from the group consisting of amino acids 1–260 of SEQ ID NO: 2, amino acids 28–260 of SEQ ID NO: 2, amino acids 1–260 of SEQ ID NO: 4, and amino acids 28–260 of SEQ ID NO: 4.

2. An isolated nucleic acid segment selected from the group consisting of nucleotides 796–1572 of SEQ ID NO: 1, nucleotides 874–1572 of SEQ ID NO: 1, nucleotides 796–1572 of SEQ ID NO: 3, and nucleotides 874–1572 of SEQ ID NO: 3.

3. A vector which comprises the nucleic acid segment according to claim 1 or 2.

4. A vector according to claim 3 which is the plasmid vector pAE1 (NCIMB 40732).

5. A vector which comprises the nucleic acid segment according to claim 1 or 2 and which is an expression vector capable of mediating the expression of the nucleic acid segment.

6. An isolated host cell comprising the vector according to claim 3.

7. A process for production of a polypeptide which is a *Helicobacter pylori* antigen, which comprises culturing a host cell transformed with an expression vector according to claim 6 under conditions whereby said polypeptide is produced, and recovering said polypeptide.

8. A composition comprising a nucleic acid segment according to claim 1 or 2 and a pharmaceutically acceptable carrier or diluent.

* * * * *